(12) United States Patent
Suzuki

(10) Patent No.: US 8,548,235 B2
(45) Date of Patent: Oct. 1, 2013

(54) SIGNAL PROCESSING APPARATUS AND STILL IMAGE GENERATION METHOD

(75) Inventor: Tatsuhiko Suzuki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/594,080

(22) Filed: Aug. 24, 2012

(65) Prior Publication Data

US 2013/0058573 A1 Mar. 7, 2013

Related U.S. Application Data

(63) Continuation of application No. PCT/JP2011/062904, filed on Jun. 6, 2011.

(30) Foreign Application Priority Data

Jun. 7, 2010 (JP) ................................. 2010-130157

(51) Int. Cl.
*G06K 9/00* (2006.01)

(52) U.S. Cl.
USPC ......................................................... 382/167

(58) Field of Classification Search
USPC ................ 382/162, 167, 255, 260, 264, 274, 382/275; 348/241, 143, 252, 300, 220.1, 348/229.1, 607, 627, 671
See application file for complete search history.

(56) References Cited

U.S. PATENT DOCUMENTS

| 5,617,136 A | 4/1997 | Iso et al. ........................... 348/71 |
| 7,714,919 B2* | 5/2010 | Inoue et al. .................... 348/300 |
| 8,077,239 B2* | 12/2011 | Inoue et al. .................... 348/300 |
| 8,098,948 B1* | 1/2012 | Tzur et al. ...................... 382/255 |
| 2006/0127084 A1 | 6/2006 | Okada ............................ 396/439 |

FOREIGN PATENT DOCUMENTS

| EP | 1 672 914 A2 | 6/2006 |
| JP | 07-289507 | 11/1995 |
| JP | 11-285019 | 10/1999 |
| JP | 2002-247444 | 8/2002 |
| JP | 2006-174069 | 6/2006 |
| JP | 2007-312832 | 12/2007 |

OTHER PUBLICATIONS

International Search Report dated Jul. 12, 2011 issued in PCT/JP2011/062904.

* cited by examiner

*Primary Examiner* — Anh Do
(74) *Attorney, Agent, or Firm* — Scully, Scott, Murphy & Presser, P.C.

(57) ABSTRACT

A signal processing apparatus includes a first image memory that stores input moving images, a noise reduction section that outputs noise-free images, an image switching section that selects and outputs one image of the input moving image and the output of the first image memory, and a freeze control section that reads, images corresponding to two or more screens including the screen with the smallest amount of blur of each screen of the input moving image based on a separated luminance signal and necessary to remove noise from the first image memory, causes the image switching section to output the images, and causes noise-free images using the images corresponding to the two or more screens including the screen with the smallest amount of blur to be consecutively outputted.

7 Claims, 5 Drawing Sheets

SIGNAL PROCESSING APPARATUS AND STILL IMAGE GENERATION METHOD

CROSS REFERENCE TO RELATED APPLICATION

This application is a continuation application of PCT/JP2011/062904 filed on Jun. 6, 2011 and claims benefit of Japanese Application No. 2010-130157 filed in Japan on Jun. 7, 2010, the entire contents of which are incorporated herein by this reference.

BACKGROUND OF INVENTION

1. Field of the Invention

The present invention relates to a signal processing apparatus and a still image generation method capable of generating a blurless still image.

2. Description of the Related Art

Conventionally, various apparatuses that electronically pick up object images using a solid image pickup device are being developed. For example, image pickup apparatuses using a CCD (charge coupled device) are also used for electronic endoscope apparatuses or the like. Electronic endoscopes can display a moving image in real time on a color monitor and cause less fatigue of operators who operate the endoscopes, and are therefore widely used.

An electronic endoscope includes an image memory that stores images obtained by picking up an image of an object. Use of this image memory allows not only moving images but also still images to be displayed. When an operator presses a freeze switch in an operation section of a scope to see a still image, writing to the image memory is interrupted and a still image is displayed on a monitor.

The output of an image pickup device that performs electronic image pickup contains random noise. Deterioration of image quality due to such random noise hardly stands out in a moving image, but it does stand out in a still image. Thus, for example, a cyclic noise reduction circuit that removes noise using correlation in the time-axis direction may be adopted (e.g., Japanese Patent Application Laid-Open Publication No. 2007-312832).

SUMMARY OF THE INVENTION

A signal processing apparatus according to an aspect of the present invention includes a first image memory that stores input moving images corresponding to a plurality of screens, a noise reduction section that removes noise from the images corresponding to the plurality of screens and outputs noise-free images, an image switching section that selects and outputs one image of the input moving image and the output of the first image memory, a Y/C separation section that separates the image from the image switching section into a luminance signal and a color signal, and gives the separated luminance signal and color signal to the noise reduction section, a second image memory that stores images corresponding to at least one screen from the noise reduction section, a blur amount calculation section that calculates an amount of blur of each screen of the input moving image based on the luminance signal separated by the Y/C separation section, a blur amount storage section that stores the amount of blur calculated by the blur amount calculation section in association with each screen of the input moving image, and a freeze control section that reads, when a freeze instruction is generated, images of two or more screens including the screen with a smallest amount of blur based on the amount of blur stored in the blur amount storage section and necessary to remove noise in the noise reduction section from the first image memory, causes the image switching section to output the images, and controls the second image memory to consecutively output noise-free images using the images corresponding to the two or more screens including the screen with the smallest amount of blur through the noise reduction section.

A still image generation method according to an aspect of the present invention includes a first image memory storing input moving images corresponding to a plurality of screens, an image switching section selecting and outputting one image of the input moving image and the output of the first image memory, a noise reduction section removing noise from the images corresponding to the plurality of screens from the image switching section and outputting noise-free images, a Y/C separation section separating the image from the image switching section into a luminance signal and a color signal and supplying the separated luminance signal and color signal to the noise reduction section, a second image memory storing noise-free images corresponding to at least one screen, a blur amount calculation section calculating an amount of blur of each screen of the input moving image based on the luminance signal separated by the Y/C separation section, a blur amount storage section storing the amount of blur in association with each screen of the input moving image, and a freeze control section reading, when a freeze instruction is generated, images of two or more screens including the screen with a smallest amount of blur based on the amount of blur and necessary to remove noise in the noise reduction section from the first image memory, causing the image switching section to output the images, and controlling the second image memory to consecutively output noise-free images using the images corresponding to the two or more screens including the image with the smallest amount of blur through the noise reduction section.

DETAILED DESCRIPTION OF THE PREFERRED EMBODIMENT(S)

Hereinafter, embodiments of the present invention will be described in detail with reference to the accompanying drawings.

(First Embodiment)

Figure 1:
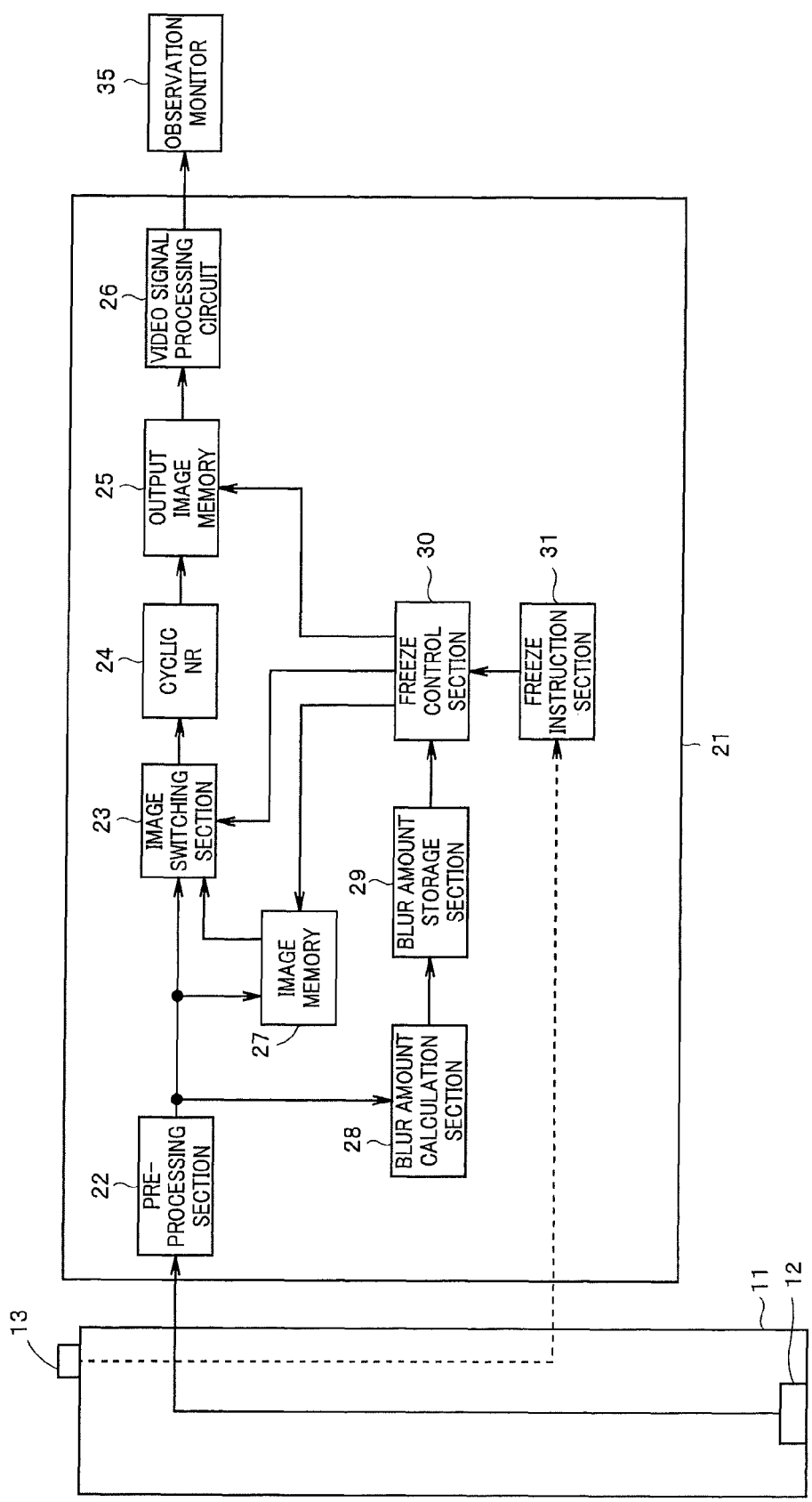
FIG. 1 is a block diagram illustrating a signal processing apparatus according to a first embodiment of the present invention.

FIG. 1 is a block diagram illustrating a signal processing apparatus according to a first embodiment of the present invention.

The present embodiment will describe an example in which the present invention is applied to an endoscope apparatus.

In FIG. 1, an endoscope 11 is provided with a solid image pickup device 12 at a distal end of an elongated insertion portion. For example, a CCD is used as the solid image pickup device 12 and the solid image pickup device 12 is designed to pick up an image of an object and output an image pickup signal. The image pickup signal from the solid image pickup device 12 is supplied to a pre-processing section 22 that constitutes a signal processing apparatus 21.

The pre-processing section 22 converts the inputted image pickup signal to a digital image signal and outputs the image pickup signal to an image switching section 23, an image memory 27 and a blur amount calculation section 28. The image memory 27 has a capacity for storing image signals corresponding to a predetermined number of frames, and with its writing/reading being controlled by a freeze control section 30 which will be described later, sequentially stores image signals from the pre-processing section 22 in frame units and outputs the stored image signals to the image switching section 23 in frame units.

The image switching section 23 switches between the image signal from the pre-processing section 22 and the image signal from the image memory 27 under the control of the freeze control section 30, and outputs the selected image signal to a cyclic NR (noise reduction circuit) 24.

Figure 2:
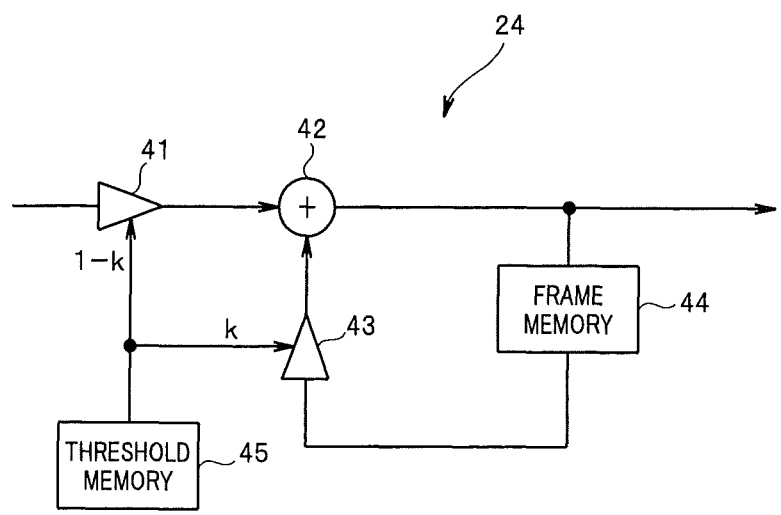
FIG. 2 is a circuit diagram illustrating an example of a specific configuration of the cyclic NR 24 in FIG. 1.

FIG. 2 is a circuit diagram illustrating an example of a specific configuration of the cyclic NR 24 in FIG. 1.

A frame-unit image signal inputted to the cyclic NR 24 is given to a multiplier 41. The multiplier 41 is given a multiplication coefficient (1−k) from a threshold memory 45, multiplies the inputted image signal by a multiplication coefficient and outputs the multiplication result to an adder 42. The output of the adder 42 is delayed by one frame in a frame memory 44 and then given to a multiplier 43. The multiplier 43 is given a multiplication coefficient k from the threshold memory 45, multiplies the inputted image signal by the multiplication coefficient and outputs the multiplication result to the adder 42.

The adder 42 applies sequential addition processing to an image signal of each frame. In this addition processing, the coefficient (1−k) is added to the image signal on the input side and the coefficient k is added to the image signal at the addition output. If the coefficient k is 0.5, the input image signal and the image signal of the addition result are mixed in 1:1, and random noise contained in the image signal is averaged and suppressed. Random noise is gradually decreased by repeating this addition processing.

When the multiplication coefficient k is greater than 0.5, the proportion that the output of the adder 42 is added increases and the noise reduction effect increases. When the image inputted is a still image, an image signal from which noise is sufficiently reduced is obtained by increasing k. However, when the image inputted is a moving image, a correlation between frames is relatively small, and it is therefore possible to prevent addition processing from increasing noise by reducing k.

The threshold memory 45 is configured to change the multiplication coefficient k depending on whether the inputted image signal is based on a still image or based on a moving image. This allows optimum noise reduction to be performed regardless of whether the input image is a still image or a moving image.

The present embodiment will describe an example where the cyclic NR 24 is used, but any noise reduction circuit other than the cyclic one may be used as long as it is a circuit that performs noise reduction using images corresponding to a plurality of screens.

The output of the cyclic NR 24 is given to an output image memory 25. The output image memory 25 has a capacity for storing, for example, image signals corresponding to one frame, and with its writing/reading being controlled by a freeze control section 30, stores the image signals from the cyclic NR 24 and outputs the stored image signals to a video signal processing circuit 26 in frame units.

The video signal processing circuit 26 applies predetermined video signal processing to the inputted image signal and outputs the processed signal to an observation monitor 35. The video signal processing circuit 26 performs video signal processing such as white balance adjustment and γ correction. The observation monitor 35 is configured to display an image on a display screen based on the inputted image signal.

The present embodiment is provided with the blur amount detection section 28 that detects the amount of blur of the image outputted from the pre-processing section 22. The blur amount detection section 28 is given the image signal from the pre-processing section 22 and calculates the amount of blur per frame. For example, the blur amount detection section 28 can detect a variation in pixels between preceding and following fields within the same frame as the amount of blur. For example, the blur amount detection section 28 may check an increment or decrement in pixel values between pixels neighboring in the horizontal direction of the preceding and following fields, accumulate the number of neighboring pixels matching in the increment or decrement between the preceding and following fields by an amount corresponding to one screen and calculate the amount of blur based on the accumulated value. It is assumed that the greater the accumulated value is, the smaller the blur of the image is. The method of calculating the amount of blur in the blur amount detection section 28 is not limited to this, but for example, the blur amount calculation section 28 may calculate the amount of blur according to an accumulated value of differences in pixel values.

The amount of blur calculated by the blur amount detection section 28 per frame is given to a blur amount storage section 29. The blur amount storage section 29 stores the amount of blur per frame in association with each frame.

In the present embodiment, the freeze control section 30 is configured to control each section using a freeze signal from a freeze instruction section 31. The freeze instruction section 31 is given an operation signal based on the operation of a freeze button 13 provided, for example, in the endoscope 11 to generate a freeze signal.

The freeze control section 30 causes the image switching section 23 to select an image signal from the pre-processing section 22 and supply the image signal to the cyclic NR 24 until a freeze signal is generated. In this way, moving image signals based on an image picked up by the endoscope 11 are sequentially supplied to the cyclic NR 24 and the cyclic NR 24 removes noise from the moving image signal and outputs the moving image signal.

On the other hand, when a freeze signal is generated, the freeze control section 30 reads an image with a small amount of blur from the image memory 27 based on the amount of blur of each frame stored in the blur amount storage section 29, and controls the image switching section 23 to give the image to the cyclic NR 24.

For example, the freeze control section 30 selects an image signal of a frame with the smallest amount of blur (hereinafter referred to as "minimum blur image") from among images of respective frames (frame images) stored in the image memory 27 at the time a freeze signal is generated, and causes the image switching section 23 to output the image signal. In this case, the freeze control section 30 may also determine a range of period during which a minimum blur image is selected in consideration of the number of frames stored in the image memory 27 and the number of frames used by the cyclic NR 24 for noise reduction. For example, a frame image with the smallest amount of blur may be selected from among frame images for a predetermined period before generation of a freeze signal of frame images stored in the image memory 27. Furthermore, a range of period during which a frame image with the smallest amount of blur is selected may be determined so that a time difference between the frame of an image selected as a minimum blur image and an input frame at the time of freeze instruction falls within a predetermined threshold.

The output image memory 25 sequentially takes in and outputs the outputs of the cyclic NR 24, and can thereby output moving images, and also consecutively outputs stored images without taking in the outputs of the cyclic NR 24, and can thereby output still images.

The noise reduction processing of the cyclic NR 24 requires a time based on the number of frames used for noise reduction. Thus, the freeze control section 30 controls the writing/reading of the output image memory 25 and determines images to be outputted during the noise reduction processing.

Figure 3:
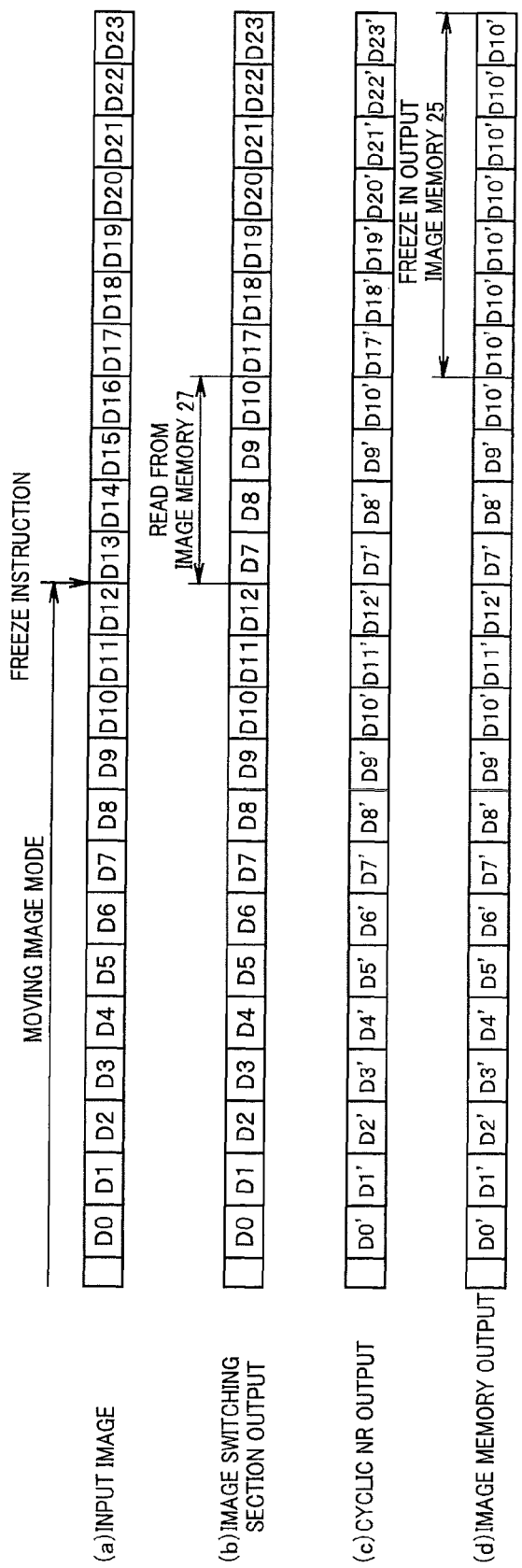
FIG. 3 is a timing chart illustrating operation of the first embodiment.

Next, the operation of the embodiment configured as shown above will be described with reference to the timing chart in FIG. 3. FIG. 3(a) shows an input image (moving image) from the pre-processing section 22, FIG. 3(b) shows an output image of the image switching section 23, FIG. 3(c) shows an output image of the cyclic NR 24 and FIG. 3(d) shows an output image of the output image memory 25. FIG. 3 shows a frame image D by each frame and shows a frame number by a subscript, and a smaller subscript number indicates an earlier frame in time. In FIG. 3, frame images D having the same subscript number indicate images based on the same frame. The apostrophe attached to the subscript number in FIG. 3 indicates that a frame image is changed through noise reduction processing.

An image pickup signal from the endoscope 11 is given to the pre-processing section 22. The pre-processing section 22 converts the image pickup signal to a digital image signal. The image signal of each frame from the pre-processing section 22 is supplied to the image switching section 23, the image memory 27 and the blur amount calculation section 28.

Now, suppose a moving image mode is set in which an image signal based on a moving image from the endoscope is outputted. In this case, the freeze control section 30 controls the image switching section 23 to give the moving image signal from the pre-processing section 22 to the cyclic NR 24. Image signals are sequentially outputted from the pre-processing section 22 in frame units. In FIG. 3, suppose no processing delay in each section is considered. As shown in FIGS. 3(a) to (d), in the moving image mode, the output of the pre-processing section 22 (FIG. 3(a)) is sequentially outputted via the image switching section 23, the cyclic NR 24 and the output image memory 25.

In the present embodiment, the output of the pre-processing section 22 is supplied to and stored in the image memory 27 and also supplied to the blur amount calculation section 28. The blur amount calculation section 28 calculates the amount of blur of each frame image based on the image signal of each sequentially inputted frame. The amount of blur calculated by the blur amount calculation section 28 is given to the blur amount storage section 29 and stored in correspondence with each frame.

Here, suppose a still image is displayed, for example, by operating the freeze button 13 of the endoscope 11. For example, suppose the freeze button 13 is operated at timing of the freeze instruction in FIG. 3 and a freeze signal is supplied to the freeze control section 30 from the freeze instruction section 31.

The image memory 27 stores frame images corresponding to a predetermined number of frames and the freeze control section 30 selects a frame image with a small amount of blur from among the frame images stored in the image memory 27 based on the amount of blur stored in the blur amount storage section 29. For example, the freeze control section 30 selects a frame image with the smallest amount of blur as a minimum blur image from among frame images later than the start frame by the number of frames necessary for noise reduction processing in the cyclic NR 24 out of the frame images stored in the image memory 27.

When, for example, the image memory 27 stores frame images from a frame image D1 in FIG. 3(a) onward, if the number of frames necessary for noise reduction processing in the cyclic NR 24 is four, a minimum blur image is selected from among frame images from a frame image D4 onward.

The example in FIG. 3 shows a case where the freeze control section 30 selects a frame image D10 as the minimum blur image when the number of frames necessary for noise reduction processing in the cyclic NR 24 is four.

When a freeze instruction is generated, the freeze control section 30 sequentially reads frame images earlier than the minimum blur image by the number of frames necessary for noise reduction processing in the cyclic NR 24. For the period necessary for the noise reduction processing of the cyclic NR 24, the freeze control section 30 causes the image switching section 23 to select an image signal from the image memory 27, and the minimum blur image and the frame images necessary for the noise reduction are sequentially read in order of frames and supplied to the cyclic NR 24 via the image switching section 23.

In the example in FIG. 3, frame images are sequentially read starting from the frame image D7 and the respective images are sequentially supplied to the cyclic NR 24 via the image switching section 23. The cyclic NR 24 applies cyclic noise reduction processing to frame images sequentially inputted. The output of the cyclic NR 24 is outputted via the output image memory 25. Thus, as shown in FIG. 3(c), images from the frame image D7 onward are sequentially outputted from the cyclic NR 24 after the freeze instruction. At a point in time at which the minimum blur image (frame image D10 in FIG. 3) is outputted from the cyclic NR 24, noise of the minimum blur image is sufficiently reduced.

Once the minimum blur image whose noise is sufficiently reduced through the noise reduction processing by the cyclic NR 24 is outputted, the minimum blur image is stored in the output image memory 25 from then on and the minimum blur image is consecutively outputted from the output image memory 25. The minimum blur image is outputted as a still image in this way (FIG. 3(d)).

The image signal from the output image memory 25 is subjected to video signal processing in the video signal processing circuit 26, and then supplied to and displayed on the observation monitor 35. In the example in FIG. 3, even when a freeze instruction is generated at input timing of a frame image D12, the frame image D10 with a smaller amount of blur is selected as a minimum blur image and this frame image D10 is subjected to noise reduction in the cyclic NR 24 and then outputted.

Thus, the present embodiment can obtain a still image of high image quality by removing blur and noise.

The above embodiment has described an example where a still image from which blur and noise are removed is displayed, but the still image obtained may also be recorded and processed. Furthermore, an example is described in FIG. 3 where four frame images are used for noise reduction, but the number of frames used for noise reduction can be set as appropriate.

As the frame image used for noise reduction, a frame image approximate in time to the minimum blur image is preferably used. It is sufficient that, as a result of noise reduction, a minimum blur image may be eventually outputted and the invention may also be configured so that noise reduction is performed using frame images later in time than the minimum blur image.

(Second Embodiment)

Figure 4:
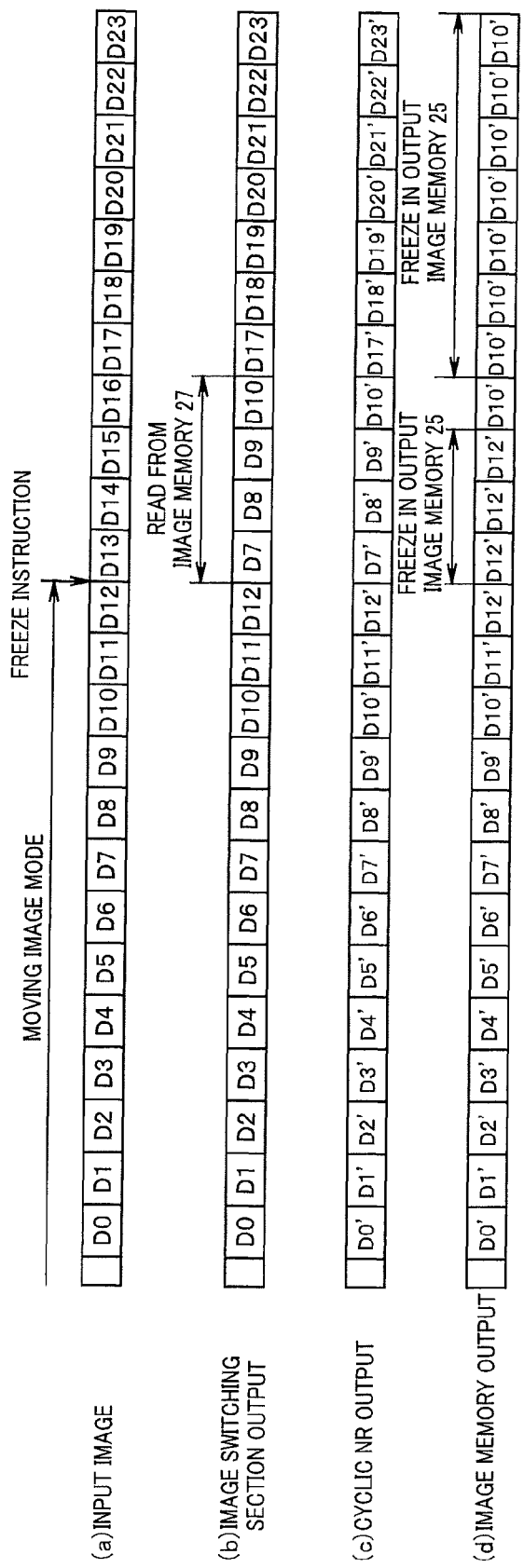
FIG. 4 is a timing chart illustrating a second embodiment of the present invention.

FIG. 4 is a timing chart illustrating a second embodiment of the present invention. A hardware configuration of the present embodiment is similar to that of the first embodiment and the present embodiment is only different from the first embodiment in the control of the freeze control section 30.

FIG. 4 is a timing chart using the same notation as that in FIG. 3, FIG. 4(a) shows an input image (moving image) from the pre-processing section 22, FIG. 4(b) shows an output image of the image switching section 23, FIG. 4(c) shows an output image of the cyclic NR 24 and FIG. 4(d) shows an output image of the output image memory 25.

The present embodiment is only different in the control over the output image memory 25 by the freeze control section 30.

In the first embodiment, although a freeze instruction is generated, the output image memory 25 sequentially outputs frame images earlier than the freeze instruction. That is, moving images are outputted even after the freeze instruction. In contrast, in the present embodiment, still images are displayed after the freeze instruction.

In this case, the noise reduction processing using a plurality of images requires a processing time corresponding to the number of frames used for noise reduction processing. Thus, in the present embodiment, frame images stored in the output image memory 25 are consecutively outputted when a freeze instruction is generated until a minimum blur image is outputted through the noise reduction processing.

FIG. 4 shows that a freeze instruction is generated when a frame image D12 is inputted. FIG. 4 as well as FIG. 3 shows an example where D10 is selected as a minimum blur image and frame images of four frames are used for noise reduction processing. That is, after a freeze instruction is generated, a frame image D7 is read from the image memory 27 as shown in FIG. 4(b) and given to the cyclic NR 24. The cyclic NR 24 performs noise reduction processing and outputs frame images D7, D8, . . . , D10. The output image memory 25, under the control of the freeze control section 30, consecutively outputs the frame image D12 already stored without storing the output of the cyclic NR 24 until the noise reduction processing on the minimum blur image D10 from the cyclic NR 24 is finished. When the minimum blur image D10 is outputted from the cyclic NR 24, the output image memory 25 consecutively outputs the minimum blur image D10 from then on.

Thus, the present embodiment can also obtain effects similar to those of the first embodiment. Furthermore, the present embodiment outputs a still image upon generation of a freeze instruction, and thereby prevents an unintended moving image from being outputted and enables operation free of uncomfortable feeling.

The present embodiment has described an example where a latest frame image stored in the output image memory 25 is consecutively outputted immediately after a freeze instruction, but other frame images may also be consecutively outputted. For example, when the output image memory 25 has a storage capacity for a plurality of frames, it is possible to output an arbitrary frame image as a still image, output a minimum blur image immediately after the freeze instruction and output a minimum blur image from which noise is gradually removed every time noise reduction processing is performed.

(Third Embodiment)

Figure 5:
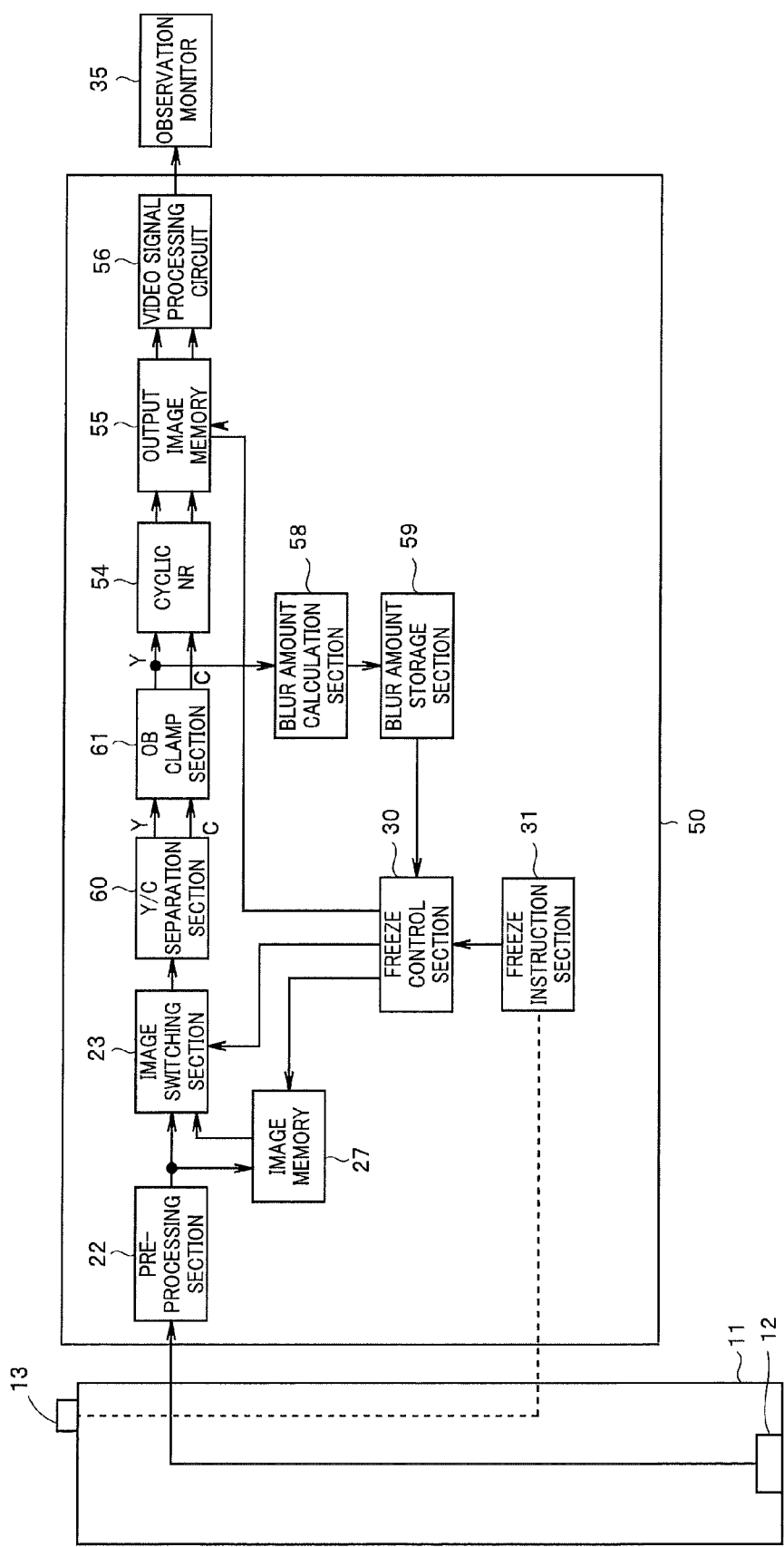
FIG. 5 is a block diagram illustrating a third embodiment of the present invention.

FIG. 5 is a block diagram illustrating a third embodiment of the present invention. In FIG. 5, components identical to those in FIG. 1 will be assigned the same reference numerals and descriptions thereof will be omitted.

The present embodiment is an example where the present invention is applied to a signal processing apparatus that Y/C-separates and processes an inputted image signal. An image signal from a simultaneous type image pickup apparatus may be inputted to a signal processing apparatus 50. In this case, it is necessary to perform Y/C separation processing of separating the inputted image signal into a luminance signal and a color signal. The present embodiment is applied to such a case.

The signal processing apparatus 50 in the present embodiment is different from the signal processing apparatus 21 in FIG. 1 in adopting a Y/C separation section 60 and an OB clamp section 61 and also adopting a cyclic NR 54, an image memory 55, a video signal processing circuit 56 and a blur amount calculation section 58 and a blur amount storage section 59 instead of the cyclic NR 24, the output image memory 25, the video signal processing circuit 26, the blur amount calculation section 28 and the blur amount storage section 29.

As the solid image pickup device 12, for example, an image pickup device adopting a color filter such as Bayer array may be adopted. The Y/C separation section 60 is given an image signal from the pre-processing section 22 via the image switching section 23 and separates the image signal into a luminance signal (Y) and a color signal (C).

The luminance signal and the color signal from the Y/C separation section 60 are given to the OB clamp section 61. The OB clamp section 61 applies OB clamp processing to the luminance signal and the color signal. The luminance signal and the color signal from the OB clamp section 61 are supplied to the cyclic NR 54. Furthermore, the luminance signal from the OB clamp section 61 is also supplied to the blur amount calculation section 58.

The cyclic NR 54, the image memory 55 and the video signal processing circuit 56 have configurations similar to those of the cyclic NR 24, the output image memory 25 and the video signal processing circuit 26, and are different only in the processing on the luminance signal and the color signal.

In the present embodiment, the blur amount calculation section 58 calculates the amount of blur of an image using the luminance signal from the OB clamp section 61. The output of the blur amount calculation section 58 is supplied to and stored in the blur amount storage section 59. The rest of the configurations of the blur amount calculation section 58 and the blur amount storage section 59 are similar to those of the blur amount calculation section 28 and the blur amount storage section 29.

The operation of the present embodiment configured as shown above is similar to that of the first embodiment except that the luminance signal and the color signal are processed separately in circuits from the Y/C separation section 60 onward and that the blur amount calculation section calculates the amount of blur based on the luminance signal from the OB clamp section 61.

The present embodiment also performs operation similar to that in FIG. 3 or FIG. 4. That is, an image with a minimum amount of blur calculated in the blur amount calculation section 58 is selected as a minimum blur image from among frame images corresponding to a predetermined period of images stored in the image memory 27 earlier than a freeze instruction, images corresponding to a predetermined number of frames including the minimum blur image are supplied to the cyclic NR 54 and noise of the minimum blur image is removed.

Furthermore, the present embodiment is configured so that the image memory 27 stores image signals before Y/C separation. This makes it possible to obtain a still image from which blur and noise are reduced using a small capacity of memory.

The above-described respective embodiments have described examples where blur amount calculation and noise reduction are performed in frame units corresponding to one screen, but such processing may also be performed in field units corresponding to one screen.

What is claimed is:

1. A signal processing apparatus comprising:
    a first image memory that stores input moving images corresponding to a plurality of screens;
    a noise reduction section that removes noise from the images corresponding to the plurality of screens and outputs noise-free images;
    an image switching section that selects and outputs one image of the input moving image and the output of the first image memory;
    a Y/C separation section that separates the image from the image switching section into a luminance signal and a color signal and gives the separated luminance signal and color signal to the noise reduction section;
    a second image memory that stores images from the noise reduction section corresponding to at least one screen;
    a blur amount calculation section that calculates an amount of blur of each screen of the input moving image based on the luminance signal separated by the Y/C separation section;
    a blur amount storage section that stores the amount of blur calculated by the blur amount calculation section in association with each screen of the input moving image; and
    a freeze control section that reads, when a freeze instruction is generated, images corresponding to two or more screens including the screen with a smallest amount of blur based on the amount of blur stored in the blur amount storage section and necessary to remove noise in the noise reduction section from the first image memory, causes the image switching section to output the images, and controls the second image memory so as to consecutively output noise-free images using the images corresponding to the two or more screens including the screen with the smallest amount of blur through the noise reduction section.

2. The signal processing apparatus according to claim 1, wherein the freeze control section reads an image of a screen stored in the first image memory earlier in time than the screen with the smallest amount of blur from the first image memory and causes the image to be outputted from the image switching section.

3. The signal processing apparatus according to claim 1, wherein the freeze control section reads an image of a screen stored in the first image memory later in time than the screen with the smallest amount of blur from the first image memory and causes the image to be outputted from the image switching section.

4. The signal processing apparatus according to claim 1, wherein the freeze control section controls the second image memory to cause the image outputted from the noise reduction section to be outputted from the second image memory for a period required for noise removing processing in the noise reduction section after the freeze instruction.

5. The signal processing apparatus according to claim 1, wherein the freeze control section controls the second image memory to cause the image of the same screen stored in the second image memory to be consecutively outputted for a period required for noise removing processing in the noise reduction section after the freeze instruction.

6. The signal processing apparatus according to claim 1, wherein the blur amount calculation section accumulates a number of neighboring pixels neighboring in a horizontal direction having the same increments/decrements of pixel values between preceding and following screens of the input moving image within the screen and calculates an amount of blur based on the accumulation result.

7. A still image generation method comprising:
    storing input moving images corresponding to a plurality of screens in a first image memory;
    selecting and outputting, using an image switching section, one image of the input moving image and the output of the first image memory;
    removing noise, using a noise reduction section, from the images corresponding to the plurality of screens from the image switching section and outputting noise-free images;
    separating the image, using a Y/C separation section, from the image switching section into a luminance signal and a color signal and supplying the separated luminance signal and color signal to the noise reduction section;
    storing noise-free images corresponding to at least one screen in a second image memory;
    calculating an amount of blur of each screen of the input moving image based on the luminance signal separated by the Y/C separation section;
    storing the calculated amount of blur in association with each screen of the input moving image; and
    reading, when a freeze instruction is generated, images corresponding to two or more screens including the screen with a smallest amount of blur based on the amount of blur and necessary to remove noise in the noise reduction section from the first image memory, causing the image switching section to output the images, and controlling the second image memory to consecutively output noise-free images using the images corresponding to the two or more screens including the image with the smallest amount of blur through the noise reduction section.

* * * * *